United States Patent [19]

Haque et al.

[11] Patent Number: 5,945,116
[45] Date of Patent: Aug. 31, 1999

[54] COMPOSITIONS FOR THE PREVENTION AND TREATMENT OF WARTS, SKIN BLEMISHES AND OTHER VIRAL-INDUCED TUMORS

[75] Inventors: Malika H. Haque; Azeez U. Haque, both of Columbus, Ohio

[73] Assignee: Haque, Inc., Columbus, Ohio

[21] Appl. No.: 08/960,303

[22] Filed: Oct. 29, 1997

Related U.S. Application Data

[60] Provisional application No. 60/030,307, Nov. 5, 1996.

[51] Int. Cl.$^6$ ..................................................... A61K 35/78
[52] U.S. Cl. ........................ 424/430; 424/195.1; 514/967
[58] Field of Search ................................ 424/430, 195.1; 514/967

[56] References Cited

U.S. PATENT DOCUMENTS

| | | | |
|---|---|---|---|
| 5,532,215 | 7/1996 | Lexdey et al. | 514/8 |
| 5,541,058 | 7/1996 | Kreider et al. | 435/5 |
| 5,562,900 | 10/1996 | Boyer et al. | 424/115 |

OTHER PUBLICATIONS

Principles and Practice of Pediatrics, Second Edition, J.B. Lippincott Company, 1994, chapter 35, p. 903.
Atlas of Pediatric Dermatology, Lumps and Bumps, Wolfe, 1993, pp. 5.5–5.7.
Color Textbook of Pediatric Dermatology, Second Edition, Viral Infections, Mosby, 1996, pp. 121–127.
Rudolph's Pediatrics, 20th Edition, Viral Infections, Simon & Shuster Company, 1996, p. 937–938.
Printed advertisement for Occlusal–HP, www.genderm.com, GenDerm Corporation, 1996.
Copy of label and instructions for DuoFilm, Schering–lough HealthCare Products, 1995.
Brochure for DuoFilm, Schering–Plough Health Care Products, Inc., 1996.

*Primary Examiner*—Jyothsna Venkat
*Attorney, Agent, or Firm*—Donald O. Nickey; Standley & Gilcrest

[57] ABSTRACT

The present invention provides a method for the prevention and treatment of viral-induced tumors, more specifically, human warts. The method uses sandal soap and/or derivatives from the sandal soap to prepare medicaments for the prevention and treatment of viral-induced tumors (i.e., warts caused by the human papillomavirus (HPV)) in humans. The method of the invention comprises the topical administration of the sandal soap or a composition derived therefrom to the human epidermis and/or to the genital tract as needed. The present invention is also concerned with a unique antiviral composition useful for topical application. The antiviral composition according to this invention is also effective against other DNA viruses such as the DNA pox virus that causes Molluscum contagiosum and may be effective against other DNA viruses such as AIDS virus and RNA viruses and may be effective against genital warts and HPV of the genital tract in infected females and are also disclosed herein. Sandal soap or a composition derived from sandal soap, is also effective in preventing dryness of the skin, rashes and flakiness associated with seborrheic dermatitis, psoriasis and allergic or eczematous rashes of the skin. This soap is also effective in the treatment of acne lesions of the face and the body and in the eradication of pustular acne lesions caused by staphylococcal acne and streptococcal bacterial infections.

7 Claims, No Drawings

COMPOSITIONS FOR THE PREVENTION AND TREATMENT OF WARTS, SKIN BLEMISHES AND OTHER VIRAL-INDUCED TUMORS

PRIORITY DATA

This application claims the benefit of U.S. Provisional Application No. 60/030,307 filed Nov. 5, 1996.

TECHNICAL FIELD

The present invention generally relates to prophylactic and therapeutic agents for the prevention and treatment of viral-induced tumors, such as warts. In one embodiment, the therapeutic agent in the form of a soap, comprising natural sandalwood oil and vegetable ingredients. The therapeutic agent may also be an isolate or isolates from the soap described herein. Use of the soap or its components as a topical agent for the prevention and treatment of viral-induced tumors, such as human papillomavirus-induced tumors, is disclosed.

BACKGROUND OF THE INVENTION

Viruses which induce tumors in mammals are widespread. Indeed, there are over sixty known types of human papillomaviruses (HPV) which are DNA viruses. These viruses can induce the production of tumors. Some of these HPV's have been associated with benign tumors, such as common warts, while others have been strongly implicated as etiologic agents in dysplasia and carcinomas in the oral and genital mucosa of the infected mammal.

Warts are a very common skin lesion in humans and are caused by various human papillomaviruses (DNA virus). Each virus is related to a specific clinical presentation of the wart. Warts are infectious and can be autoinoculated and spread to other individuals by direct contact.

Verrucae warts have a rough surface, are lumpy and typically flesh colored. Finger-like projections and sometimes dark specks are present, which are the result of thrombosed capillaries. Usually these warts are found on the face and scalp.

Plantar warts are found on the planter surface of the feet and can be deep and painful. These warts occur singularly, in clusters or be spread over a wide area.

Flat warts are typically small, flat-topped, flesh colored papules that occur primarily on the face, hands and forearms. Usually the surface of the wart is smooth and they may appear in the hundreds.

Genital warts are soft, flesh colored or slightly pigmented and occur in the genitalia of the mammal and are sexually transmitted. Chronic infections of the viruses that cause genital warts in women are a serious problem as intra epithelial neoplasia or squamous cell carcinoma may develop. See Oski et al., *Princ. Pract. Pediatrics,* 2nd ed., pp. 789–790.

There are various therapies for the treatment of warts, but none are considered truly effective as they typically fail to totally cure the lesions and do not prevent recurrence. A discussion of presently accepted therapies can be found in Stone, 1995, *Cl. Infec. Diseases*, Suppl. 20, pp. 991–997 and Sterling, 1995, *Practioner*, Jan. 239(1546), pp. 44–47. Numerous compositions are presently marketed for wart removal. One such product is OCCLUSAL®-HP marketed by the GenDerm Corporation of Lincolnshire, Ill. This product is a 17% solution of salicylic acid in a polyacrylic vehicle. The Shering-Plough Company of Memphis, Tenn. produces and markets a product known as DUO FILM® which is a patch containing salicylic acid. The product literature recommends that the wart be washed and dried prior to the application of a medicated patch which contains 40% salicylic acid. This patch is then covered with an additional bandage and the procedure is repeated every 48 hours until the wart is gone, which sometimes takes up to 12 weeks.

Recently, it has also been observed that individuals with depressed immune systems, such as sufferers of Acquired Immune Deficiency Syndrome (AIDS), are prone to HPV infections which can result in tumor growth over their entire bodies, resulting in great mental and physical distress to the afflicted individual.

Current modalities for the treatment of viral-induced tumors involve the removal of the tumor by either: (1) surgical intervention (laser or operative); (2) the application of organic acids, such as glacial acetic acid and/or salicylic acid and lactic acid to "burn" the tumor away; (3) the injection into the tumor of an anti-tumor vaccine prepared from ground tumors; and to a lesser extent, (4) the use of a drug, such as podophyllin, interferons and fluorouracil or 5-FU; and (5) freezing.

While being useful for removing the viral-induced tumor, the current treatment modalities still suffer from one or more of the following drawbacks: (1) they can result in the destruction of healthy uninfected tissue; (2) they can result in scarring and disfigurement; (3) they can result in discomfort to the mammal being treated thereby; (4) they can result in necrosis of the tumor and the surrounding tissue may can result in a secondary infection which may require treatment with an antibiotic; and (5) they do not always result in the destruction of latent viral DNA which may be maintained in surrounding tissues. Furthermore with these conventional treatments, subjects suffer from significant local, and at times, systemic side effects, incomplete resolution and frequent recurrences of the tumors, and of course, the expense incurred.

It is also known that phototherapy is used for removing laryngeal papillomatosis tumors. While such phototherapy reduces tumor growth by about 50%, it also results in a generalized skin photosensitivity for at least six weeks, as well as other minor reactions. Despite the apparent success of this technique, the presence of latent viral DNA is nonetheless still maintained in the surrounding tissues.

U.S. Pat. No. 5,073,630 discloses a polymeric anhydride of magnesium and ammonium phospholinoleate with antiviral, antineoplastic and immunostimulant properties. This antiviral agent is produced from a selected line of Aspergillus sp. However, the compound is insoluble in water and possesses a high molecular weight (316,000 daltons). Recovery of the compound from the culture is problematic and costly.

U.S. Pat. 5,562,900 discloses a composition for the treatment of viral-induced tumors comprising an Aspergillus fermentation extract or a derivative thereof in a pharmaceutically acceptable carrier.

U.S. Pat. 5,541,058 discloses an in vitro method for testing the effectiveness of antiviral agents. More specifically, this patent relates to a method for screening anti-papillomavirus drugs which can interfere with the early and maintenance stages of papillomavirus infection. The teachings of this patent are incorporated herein by reference.

U.S. Pat. 5,332,215 discloses a method for inhibiting viral proliferation by preventing or inhibiting viral replication or killing the virus on contact. The method uses serine protease inhibitors, their analogs, salts, conjugates or derivatives.

There presently exists in the medical community a need for improved methods and compositions which provide prophylactic and/or therapeutic treatment of viral-induced tumors such as warts in humans.

SUMMARY OF THE INVENTION

One aspect of the present invention relates to the use of a soap for the prevention and treatment of viral-induced tumors. Another aspect of the invention relates to the use of a component or components of said soap to prevent and treat viral-induced tumors in mammals, especially humans. One major benefit of the present inventive composition is that it neither destroys healthy, uninfected tissues nor results in either significant systemic side effects, local side effects such as initiation, necrosis of tissue surrounding the wart, allergic rashes, scarring, disfigurement or discomfort to the human treated therewith.

Another aspect of the present invention is directed to a simple method for providing prophylactic and therapeutic treatment of viral-induced tumors in humans. An additional aspect of the present invention relates to a method for the destruction of latent viral DNA which is contained in tissues so as to prevent recurrence of these tumors.

Thus, there is disclosed a method for the prevention and treatment of viral induced tumors in a mammal, said method comprising the topical application of sandal soap.

Also disclosed is a prophylactic and therapeutic composition for the prevention and treatment of viral induced tumors in mammals comprising sandal soap extract, or a derivative thereof, in a pharmaceutically accepted carrier and wherein said sandal soap extract is obtained from a soap known as Mysore Sandal soap, manufactured by Karnataka Soaps & Detergents, Ltd.

There is further disclosed a method for the prevention and treatment of genital warts and eradication of human papallomavirus from the female genital tract in infected females, comprising the application of a cream or douche derived from sandal soap to the affected area of the human body. There is also disclosed a method for preventing cancer of the cervix, said method comprising the application of sandal soap to the genital area of a female for a period of time and at a sufficient concentration to eradicate the human papallomavirns from the genital area of the female. There is also disclosed a method for the treatment and prevention of dry skin, flakiness of the skin, rashes associated with seborrheic dermatitis, psoriasis, eczematous and allergic rashes in a human, said method comprising the topical application of sandal soap or cream derived from the sandal soap to the skin of said human.

The method of this invention is specifically directed to the use of a composition that is suitable for topical application. The initial discovery of the inventors was based upon the use of a soap manufactured by Karnataka Soaps & Detergents, Ltd., Bangalore, India, known and marketed as "Mysore Sandal Soap". The product packaging states that this soap contains natural Mysore sandalwood oil distilled by the government of Karnataka. It is known that this soap also contains vegetable ingredients. A second soap manufactured by Alfa Cosmetics, of Bombay, India, known as "Eastern Mysore's Pure Sandal Soap" has also been found effective in preventing and/or treating viral induced epidermal tumors, however, it is somewhat less effective. The "Eastern Mysore's Pure Sandal Soap" lists as its ingredients: palm stearin, rice bran fatty, coconut oil, caustic soda, perfume, sandalwood oil and preservatives. As of the filing date of this application, the inventors are working towards the isolation of the active ingredient or active ingredients. As used herein and in the claims, the term "sandal soap" shall mean: (1) the actual soap products containing sandalwood oil marketed by the Alfa Cosmetics Company and/or Karnataka Soaps & Detergents Ltd., and/or (2) the active component or components derived from said sandal soap.

Sandalwood oil is a pale yellow, somewhat viscous, aromatic liquid obtained from sandalwood and is used chiefly in perfumes and soaps. Sandalwood is a close grained, fragrant, yellowish heartwood of a parasitic tree (*Santalum album* of the family Santalaceae). This tree is typically found in southern Asia and Australia. Palm stearin or palm oil is an edible fat obtained from the flesh of the fruit of several palms and is typically used in soaps and lubricating greases. More particularly, palm stearin is a fraction of palm oil. Palm oil typically contains the fatty acid palmitic acid, which is a waxy, crystalline saturated fatty acid having the formula $C_{16}H_{32}O_2$ and may exist in the free acid form or in the form of esters (as glycerides) and most fats and fatty oils, and in several essential oils and waxes. Stearic acid ($C_{18}H_{36}O_2$) is one of the most common fatty acids and occurs and glycerides in most animal and vegetable fats, particularly in the harder fats with high melting points. A solid mixture of stearic and palmitic acids, "stearine", is used for making candles. The soaps are the sodium and potassium salts of stearic and palmitic acids.

One sandal soap listed rice bran fatty as an ingredient. Grains of cereals, such as rice and wheat, have a great deal in common with each other. They consist of three major structures: (1) the embryo or germ of the new plant; (2) the endosperm, which is the storer of nutrients for the germinating plant; and (3) the protective layers of the seed coat, which are regarded as bran by the miller. A typical bran composition (wheat on a dry weight basis) is: lignin—8%, cellulose—30%, hemi-cellulose—25%, starch—10%, sugars—5%, protein—15%, lipid—5%, and inorganic and other substances making up the remainder. It is believed that the rice bran fatty component of the sandal soap is in fact the lipid component from rice bran. It is further believed that there are a number of fatty acids with unusual structures that are found in rice bran. One such fatty acid is ricinoleic acid. Coconut oil is a fatty acid oil or semi-solid fat extracted from fresh coconuts and is used especially in making soaps and food products. The fatty acid composition of coconut oil is predominantly lauric acid. The composition of coconut oil has been thoroughly characterized and is known in the art. Caustic soda, also known as sodium hydroxide, is well known to be used in the production of soaps and detergents.

Other components such as preservatives and perfumes can be used in the sandal soaps of this invention. At this time, the complete characterization of those components are not available the inventors. However, continued analysis is underway to determine the active component or components that have demonstrated outstanding utility as a method of treating or preventing human warts. In any event, as will be demonstrated below, it has been discovered that sandal soap is very effective in treating human warts.

In a further embodiment of this invention, the method of preventing or treating viral-induced tumors uses sandal soap that is in a pharmaceutically acceptable carrier such as oleaginous ointment for topical administration.

In another embodiment of this invention, the active component or components of the sandal soap are disclosed for the prevention or treatment of viral-induced tumors.

There is further disclosed a prophylactic and therapeutic composition for the prevention and treatment of viral-induced tumors in mammals comprising sandal soap extract or a derivative thereof in a pharmaceutically acceptable carrier wherein said sandal soap extract is obtained from a soap known as Mysore's Pure Sandal Soap manufactured by Alfa Cosmetics, Bombay, India and/or a soap known as Mysore Sandal Soap manufactured by Kamataka Soaps & Detergents Ltd., of Bangalore, India.

In particular, the sandal soap itself and/or the extracts (active components) of the sandal soap described herein are used for the preparation of prophylactic and therapeutic compositions for the treatment and prevention of viral-induced tumors in humans. Preferably, the compositions useful in the method are topically applied to the human in need of such therapy.

The method of the present invention neither destroys healthy, uninfected tissue nor results in any local or systemic side effects, scarring, disfigurement or discomfort to the human treated. Furthermore, the use of the present method results in the destruction of latent viral DNA found in the tumor and the surrounding tissues so that instances of incomplete resolution and tumor recurrence are prevented. The method includes the use of the sandal soap or an extract derived therefrom, for the administration to an area of the human which is anticipated to evidence viral-induced tumor growth, or an area which presently exhibits viral-induced tumor growth (i.e., warts) to prevent or eliminate the viral-induced tumor. In accordance with the method according to this invention, "regular use of the sandal soap" is meant to mean application of the sandal soap at least twice a day to the body surface containing the wart(s). A further embodiment of the method of this invention comprises washing the affected area of the body with the soap, rinsing the area and then placing a small amount of soap residue on the tumor to be treated. It has been determined through clinical evaluation that once the method of this invention is initiated, the warts begin to shrink, no matter what size, and will totally disappear after a period of two to four weeks of treatment.

DESCRIPTION OF PREFERRED EMBODIMENTS

The present invention is based, in part, on the discovery that a commercially available soap manufactured by the aforementioned companies is useful for the treatment of viral-induced tumors in humans.

The initial chemical analysis was conducted as follows. 2.5 g of the sandal soap was dissolved in 15 ml of purified water. The pH was determined to be about 10.26. This solution was extracted, after acidification, with methylene chloride. The methylene chloride extract was dried over sodium sulfate and the volume was adjusted to 40 ml. The extract was diluted 10-fold and subjected to Gas Chromatography Mass Spectrometry (GC-MS) analysis. The analysis was performed on a Finnigan Model 4500 GC/MS system equipped with an HP-5890 Series II gas chromatograph and Galaxy 2000 data system. The semi-volatile GC column was a 30 meter by 0.32 mm RTX-5 capillary column. The temperature of the column was held at 40° C. for 1 minute, and then increased at 10° C./minute to a final temperature of 270° C.

Conversion of the hydroxide ion concentration was carried out using the definition of pH $(-\log[OH^-]=14-pH)$. It was determined that the concentration of sodium hydroxide equivalents was about 0.015% by weight.

GC-MS analysis confirmed that no salicylic acid was present, a known agent for the treatment of warts. The fatty acids, dodecanoic, tetradecanoic, hexadecanoic, oleic and octadecanoic, were present. The weight ratio of dodecanoic; tetradecanoic; hexadecanoic; oleic; octadecanoic was 7:3.4:50.1:32:6.7. The ratio of hexadecanoic acid to oleic acid in palm oil is about 34 to 43% hexadecanoic acid to about 38 to 40% oleic acid. This analysis indicates that the soap was most likely derived from palm oil.

No other peaks were evident from this GC-MS analysis of the methylene chloride extract of the sandal soap at a detection limit after dilution of 1% by wt. While the presence of ricinoleic acid was not determined by this method, it is possible that a low level concentration of this or other unusual fatty acids could account for the demonstrated efficacy against human warts. Further, the components of the sandalwood oil or the rice bran oil could be effective individually or as synergistic combinations against human viral-induced tumors.

EXAMPLE 1

One inventor of the present invention is a pediatrician, actively engaged in the medical practice. Typically, pediatricians are constantly exposed to the HPV, which causes warts in humans. The inventor has had numerous occurrences of warts over the last 10 years, for which all available methods of treatment have been used, including excision using liquid nitrogen and various salicylic acid preparations. All of these methods of treatment failed to completely eradicate the warts. Typically, the warts became secondarily infected and were very painful. With conventional treatment, the warts subsided, however they only returned after a period of time. This inventor also developed a painful wart in between her fourth and fifth toes of her right foot which were scraped and then treated with commercially available creams known as Vytone and Lachydrin by a Dermatologist. Despite continued treatment, the warts recurred and were a constant source of aggravation. The inventor also developed a large wart on her left thumb, about 3 mm in diameter with dark spots on the surface. Subsequent to the appearance of the wart on the thumb, Mysore Sandal Soap was obtained and, after 4 to 5 days of use (washing twice daily), the wart on the thumb became smaller (appeared to shrink), reduced down to about 2 mm in diameter and continued to decrease in size until it completely disappeared after three weeks of treatment.

The inventor then began to wash (twice daily) the wart on her foot, which at the beginning of therapy was about 5 mm in diameter. After one week of daily applications of the sandal soap, the pain of the tumor had decreased and the wart was beginning to shrink in size. After a second week of washing and rinsing the tumor with the sandal soap, the inventor began to leave a small amount of soap residue on the affected area. No irritation or redness resulted from the soap residue and the tumor continued to decrease in size and totally disappeared after the third week of such usage.

EXAMPLE 2

A second individual, a four (4) year old black female, presenting a huge (about 4 mm), raised, wart on her right hand, began treatment of the wart with sandal soap. After about two weeks of treatment, (washing twice a day), the tumor had reduced to a small black dot and at the third week of treatment, the tumor was completely gone.

EXAMPLE 3

A seven (7) year old white male presented warts on each foot; one being about 3 mm in diameter, with raised dark spots on the surface and the other about 4 mm labulated and flesh-colored. These tumors were washed twice daily with the sandal soap. After one week of therapy, the tumors were visibly smaller and at that time, soap residue was allowed to remain on the tumor and surrounding tissue after washing. After two weeks, the tumors were completely gone and no new tumors were evident.

EXAMPLE 4

A ten (10) year old white female presented a large, 3 mm raised and fleshy wart on the dorsum of her right hand. Administration of the sandal soap began and after two weeks of treatment, the tumor shrunk to approximately half its size.

EXAMPLE 5

5 grams of the Mysore Sandal Soap was dissolved in 15 ml of distilled water. The pH of the solution was adjusted to 5.5 with HCl and this mixture was then extracted with methylene chloride. The methylene chloride extract is dried and the volume reduced to about 20 ml. This methylene chloride extract is then topically applied to a human wart. Application is to occur twice daily. After one to two weeks of treatment, the viral-induced tumor will have been eliminated.

EXAMPLE 6

Equal parts by weight of rice bran fatty acids and sandalwood oil is prepared. A cream suitable for topical use is prepared by mixing 1 gm of the rice bran/sandal-wood oil composition with 20 gms of a balm, which comprises a mixture of petrolatum, mineral oil and wood alcohol. The cream is useful for minor irritations and in the treatment of viral infections which produce skin lesions or warts.

EXAMPLE 7

A third year medical student who had recurrence of plantar warts alter surgical removal, used the sandal soap for four (4) weeks for washing the warts and was told to leave a small residue of soap on the warts after washing. The warts started shrinking as early as the first week and they totally disappeared after the fourth (4th) week and have not recurred.

EXAMPLE 8

A sixteen (16) year old white male subject presented a plantar wart on the foot that had recurred after surgical removal. The subject began using the sandal soap and after a period of about 3 weeks, the wart was totally gone and has not recurred. This subject washed the plantar wart with the sandal soap at least twice daily.

EXAMPLE 9

A third year, white, female medical student presented warts on her fingers. She had previously used salicylic acid preparation, but the warts had recurred. After use of the sandal soap, twice daily for about 1 week, the warts started shrinking and in about three (3) weeks, the warts totally disappeared and have not recurred.

EXAMPLE 10

One adult white male had chronic seborrheic dermatitis on the face and scalp. Upon daily administration of the sandal soap to the scalp and face, a significant improvement in his dermatologic condition was obvious. He found sandal soap was more effective in treating his condition than expensive shampoos and steroid creams which he previously used.

EXAMPLE 11

An adult white male and female presented psoriasis lesions on hands and arms. After approximately 1 week of treatment with the sandal soap, great improvement in this condition resulted. Twice daily applications of the sandal soap to the affected areas, significantly reduced flaking and dryness. The use of expensive steroid creams was significantly reduced by these subjects as the sandal soap therapy significantly reduced the psoriasis lesions. This soap could also be beneficial for allergic and eczematous rashes.

EXAMPLE 12

A fifty (50) year old white female presented with a plantar wart embedded inside a callous on her right foot which had recurred after several treatments which included surgical removal, freezing, etc. by a dermatologist. After about four (4) weeks of treatment with the sandal soap, the wart was totally gone and so was the pain and discomfort, which disappeared after the total resolution of the deeply embedded plantar wart on her right foot.

At the time of filing the provisional application, upon which this application is based, further clinical work was underway to refine the method of the present invention and to further characterize the active components of the sandal soap.

At this time, a total of fifteen (15) individuals have undergone the inventive therapy and all 15 experienced the eradication of their palmar or plantar warts. The application of the sandal soap at least twice daily with occasional placement of soap residue on the warts, results in disappearance of the warts in about four (4) weeks. Deeply embedded warts took up to eight (8) weeks to resolve. Of the 15 individuals treated to date, twelve (12) were previously treated with salicylic acid preparations, liquid nitrogen or surgical techniques. In all twelve (12) cases, the warts reappeared. Upon reappearance of the warts, the subjects enrolled into the sandal soap study and have successfully completed their course of therapy and the warts have failed to reappear. It was noted that the individuals that had previously received salicylic acid treatments were slower to respond to the inventive therapy when warts were covered by scar tissue. However, in all cases, the warts had disappeared within four (4) to eight (8) weeks and recurrence of warts had not yet been detected.

EXAMPLE 13

Molluscum contagiosum is a skin disease caused by DNA pox virus and is characterized by the appearance of small, discreet lesions, in groups, on the face, arms or genitalia. The lesions are firm and pearly white with a sharply indented central core and yield an infectious filtrate which produces the disease when inoculated into human volunteers. The disease, which may be epidemic in children, occurs in all ages and is world-wide in distribution. Two subjects with Molluscum contagiosum were treated for about four (4) weeks using the sandal soap of the present invention. One of them had about twenty-five (25) large and small lesions. Some of the lesions were greater than 1 cm in diameter; the smaller lesions were about 5 mm in diameter. Application of the sandal soap occurred at least once per day, with a small amount of soap left behind on the lesions and the lesions disappeared in about four (4) weeks. The lesions failed to reappear since resolution.

EXAMPLE 14

The sandal soap according to the invention has also been found effective against the flaky rashes of psoriasis to seborrheic dermatitis, eczematous rash and dry skin. Individuals with the above recited conditions, upon use of the sandal soap, experienced a considerable decrease in itching, redness and flakiness subsequent to the use of the sandal soap. Also, the use of steroid creams was considerably reduced when the sandal soap was used in the management of the above recited rashes.

EXAMPLE 15

Adolescents and adults presented with facial acne and were instructed to use the sandal soap on a regular, daily basis. After about two (2) weeks of therapy, the presence of facial acne had decreased significantly or disappeared. Sandal soap was effective in eradicating pustular acne also. This work evidences that the sandal soap has anti-bacterial characteristics also which indicates its efficacy towards the control of Streptococcus and Staphylococcus skin infections.

EXAMPLE 16

A pediatrician colleague of the inventors, who had palmar warts for the last fourteen (14) years that kept recurring after the available, conventional treatment for warts, including use of salicylic acid preparation, used sandal soap for five (5) weeks with total resolution of the palmar wart that has not recurred.

EXAMPLE 17

A 27 year old married female with an abnormal pap smear due to HPV, as per her gynecologist, used sandal soap to wash her genital area whenever she took her bath and also sat in soapy water from sandal soap in her bathtub at least a couple of times per week. When the pap smear was repeated six (6) months later, it is reported to be normal and the HPV was not detected.

Other Indications

Since warts are caused by human papillomaviruses (HPV) of different types and the sandal soap disclosed herein can eradicate this virus, it is contemplated that this composition may be useful in methods of eradicating other viral-induced tumors. Genital warts are also caused by HPV. Genital warts in women are a genuine nuisance and are very hard to eradicate. The sandal soap may also be useful to prevent other DNA viral lesions. Its effect on other DNA as well as RNA viruses needs further investigation. The fact that sandal soap appears to be extremely effective in eradicating palmar and plantar warts caused by the DNA HPV virus and Molluscum contagiosum caused by DNA pox virus supports its effectiveness against other DNA and RNA viruses.'

It is proposed that the continued use of sandal soap or the components of sandal soap would be effective for the prophylactic treatment of viral tumors and eradication of DNA viral infections and bacterial infections caused by streptococci or staphylococci.

During the clinical evaluation of the present invention, it has come to the attention of the inventors that the sandal soap and/or the effective components of the sandal soap are also very effective in preventing dryness of the skin. As mentioned in Example I, an inventor of the present application is a pediatrician and is constantly (i.e., at least 40 times per day) washing her hands after examining a subject. This constant washing with soaps provided in the hospital setting, result in severe dryness to the hands. The sandal soap was applied twice a day to the dorsum of her left hand. The sandal soap was not applied to the dorsum of her right hand while washing her hands. At the end of approximately two weeks, the skin on the dorsum of her left hand was smooth, soft and shiny which was in contrast to the dry rough skin on the top of her right hand.

Thus, the sandal soap described herein has also been found effective in preventing the flakiness and dryness associated with skin that is constantly subject to harsh detergents. In addition, the sandal soaps have shown to be active against seborrheic dermatitis and psoriasis.

From the studies disclosed herein, sandal soap has specific antiviral properties against HPV, DNA pox virus that causes Molluscomcontagiosum and is also effective in the treatment of bacterial skin infections. The properties of sandal soap also include anti-inflammatory characteristics as it has demonstrated effective emollient properties for dry skin and psoriasis.

It is quite evident from the clinical experience to date, that the sandal soap of the present invention has been outstandingly effective in the treatment and elimination of warts. The complete eradication of the warts with no recurrence is truly a surprising result as the medical community still searches for a cost effective and efficacious method to control this human malady.

Industrial Applicability

Viral-induced tumors, especially of the skin, are very common. These tumors are typically very difficult to treat, control and prevent. The medical community has searched for decades for new therapies to treat this common human malady. The present invention provides a simple and cost-effective method to treat and prevent these viral-induced tumors.

As mentioned above, the term "sandal soap" is meant to include the soap itself, and any active component or components that are isolated therefrom. At the time of filing this patent application, the inventors are diligently pursuing the isolation of the active component or components and believe that such can be accomplished without excessive experimentation.

Many modifications may be made to the invention herein without departing from the basic spirit or scope of the invention. Accordingly, it will be appreciated by those skilled in the art, that within the scope of the appended claims, the invention may be practiced by means other than has been specifically described herein.

We claim:

1. A method for the treatment of viral-induced tumors in mammals selected from a group of consisting of verrucae warts, plantar warts, flat warts, genital warts, and Molluscum contagiosum said method comprising the topical application of a composition which comprises a mixture of rice bran fatty, coconut oil, caustic soda and sandalwood oil.

2. The method according to claim 1 wherein said mammal is a human.

3. A method according to claim 2 wherein said composition additionally comprises palm stearine.

4. The method according to claim 2 wherein said viral-induced tumors are caused by human papillomavirus (HPV).

5. The method according to claim 2 wherein said Molluscum contagiosum is caused by DNA pox virus.

6. The method according to claim 2 wherein said genital warts are in the female genital tract.

7. The method according to claim 6 wherein said composition is a cream or a douche.

* * * * *

UNITED STATES PATENT AND TRADEMARK OFFICE
CERTIFICATE OF CORRECTION

PATENT NO. : 5,945,116
DATED : August 31, 1999
INVENTOR(S) : Malika Haque and Azeez Haque It is certified that error appears in the above-identified patent and that said Letters Patent is hereby corrected as shown below:

In column 1, line 15, after "agent", please insert -- is --.

In column 2, line 30, please delete "may can" and replace it with -- and may --.

In column 3, lines 35 and 26, please delete "papallomavirus" and replace it with -- papilomavirus --.

In column 3, lines 42 and 43, please delete "papallomavirns" and replace it with -- papillomavirus --.

In column 4, line 22, please delete "occurs and" and replace it with -- occurs in --.

In column 4, line 52, after the word "able", please insert -- to --.

In column 5, line 6, please delete "Kamataka" and replace it with -- Karnataka --.

In column 5, line 61, please delete "(log|OH⁻|=14-pH|" and replace it with -- (log[OH⁻]=14-pH] --.

In column 6, line 67, please delete "labulated" and replace it with -- lobulated --.

In column 8, line 14, please delete "callous" and replace it with -- callus --.

In column 9, line 10, please delete "acne and" and replace it with "acne".

UNITED STATES PATENT AND TRADEMARK OFFICE
CERTIFICATE OF CORRECTION

PATENT NO. : 5,945,116
DATED : August 31, 1999
INVENTOR(S) : Malika Haque and Azeez Haque It is certified that error appears in the above-identified patent and that said Letters Patent is hereby corrected as shown below:

In column 10, line 13, please delete "Molluscomcontagiosum" and replace it with -- Molluscum contagiosum --.

Signed and Sealed this

Fourteenth Day of March, 2000

Attest:

Q. TODD DICKINSON

Attesting Officer

Commissioner of Patents and Trademarks